US006136322A

United States Patent [19]
Lemon et al.

[11] Patent Number: 6,136,322
[45] Date of Patent: Oct. 24, 2000

[54] HEPATITIS A VIRUS DELETION MUTANTS AND VACCINE FORMULATIONS CONTAINING THE SAME

[75] Inventors: Stanley M. Lemon; David R. Shaffer, both of Chapel Hill, N.C.

[73] Assignee: The University of North Carolina at Chapel Hill, Chapel Hill, N.C.

[21] Appl. No.: 09/094,919

[22] Filed: Jun. 15, 1998

Related U.S. Application Data

[63] Continuation of application No. 08/273,594, Jul. 11, 1994, Pat. No. 5,766,906.

[51] Int. Cl.$^7$ ................................................. C12N 15/51
[52] U.S. Cl. ................................... 424/226.1; 424/189.1; 424/204.1; 424/205.1; 424/278.1; 435/5; 435/69.3; 435/236; 435/237; 536/23.72; 514/2
[58] Field of Search ............................... 424/189.1, 204.1, 424/205.1, 226.1, 278.1; 435/5, 69.3, 236, 237; 536/23.72; 514/2

[56] References Cited

U.S. PATENT DOCUMENTS

| | | |
|---|---|---|
| 4,532,215 | 7/1985 | Daemer et al. . |
| 4,620,978 | 11/1986 | Daemer et al. . |
| 4,636,469 | 1/1987 | Daemer et al. . |
| 4,894,228 | 1/1990 | Purcell et al. . |

FOREIGN PATENT DOCUMENTS

WO 92/19268  11/1992  WIPO .

OTHER PUBLICATIONS

R.W. Jansen et al.; Mutations in the Capsid–Encoding and 5' Nontranslated Regions of the Hepatitis A Virus Genome Associated with Adaptation of Virus to Growth in Cell Culture, *Viral Hepatitis and Liver Disease* pp 36–42 (1988).
R.W. Jansen et al.; Complete Nucleotide Sequence of a Cell Culture–Adapted Variant of Hepatitis A Virus: Comparison with Wild–Type Virus with Restricted Capacity for in Vitro Replication *Virology* 163:299–307 (1988).
G. Siegl and S.M. Lemon; Recent advances in hepatitis A vaccine development *Virus Research* 17:75–92 (1990).
G.M. Duke et al.; Attenuation of Mengo virus through genetic engineering of the 5' noncoding poly(C)tract *Nature* 343:474–476 (1990).
S.M. Lemon et al.; Antigenic and Genetic Variation in Cytopathic Hepatitis A Virus Variants Arising during Persistent Infection: Evidence for Genetic Recombination *Journal of Virology* 65:2056–2065 (1991).
K.L.Taylor et al.; Attenuation Phenotype of a Cell Culture— Adapted Variant of Hepatitis A Virus (HM175/p16) in Susceptible New World Owl Monkeys *The Journal of Infectious Diseases* 168:592–601 (1993).
Abstract: D.Shaffer et al.; Structure and Function of a Pyrimidinerish Tract Within the 5' Nontranslated Region of Hepatitis A virus RNA, P19–2, p. 177 (Aug. 1993).
J.I. Cohen et al.; Complete nucleotide sequence of an attenuated hepatitis A virus: Comparison with wild–type virus, *Proc. Natl. Acad. Sci. USA* 84:2497–2501 (1987).
E.A. Brown et al.; In Vitro Characterization of an Internal Ribosomal Entry Site (IRES) Present within the 5' Nontranslated Region of Hepatitis A Virus RNA: Comparison with the IRES of Encephalomyocarditis Virus, *J. of Virology*, 68, No. 2:1066–1074 (1994).
B.C. Ross et al.; Molecular Cloning of cDNA from Hepatitis A Virus Strain HM–175 after Multiple Passages in vivo and in vitro, *J. Gen. Virol.* 67:1741–1744 (1986).
D.R. Shaffer et al.; Large Deletion Mutations Involving the First Pyrimidine–Rich Tract of the 5' Nontranslated RNA of Human Hepatitis A Virus Define Two Adjacent Domains Associated with Distinct Replication Phenotypes, *J. of Virology* 68, No. 9:5568–5578 (1994).

*Primary Examiner*—Laurie Scheiner
*Attorney, Agent, or Firm*—Myers Bigel Sibley & Sajovec

[57] ABSTRACT

Disclosed are live hepatitis A virus deletion mutants having a deletion mutation in the 5' nontranslated region of the viral genome. The deletion mutation may be selected from the group consisting of (a) pY1 deletion mutations that cause the virus to retain the ability to replicate in monkey kidney cells; and (b) deletion mutations between nucleotides 140 and 144 that render the virus temperature sensitive. Advantageously, the deletion mutation may be an attenuating mutation. Pharmaceutical formulations containing such viruses are disclosed, along with the use thereof to produce antibodies useful for diagnostic purposes and for imparting protective immunity against hepatitis A virus.

9 Claims, 4 Drawing Sheets

| | 31 °C | 35.5 °C |
|---|---|---|
| Wild-type | | |
| pP16-pY | + | + |
| pP35-pY | n.d. | + |
| pΔ99-115 | n.d. | + |
| pΔ99-130 | n.d. | + |
| pΔ99-134 | n.d. | + |
| pΔ96-134 | n.d. | + |
| pΔ93-134 | − | − |
| pΔ96-137 | n.d. | + |
| pΔ96-139 | n.d. | + |
| pΔ96-140 | n.d. | + |
| pΔ96-141 | n.d. | + |
| pΔ99-144 | + | − |
| pΔ116-144 | + | − |
| pΔ31-144 | + | + |

```
                90        100       110       120       130       140       150       160
                |         |         |         |         |         |         |         |
Wild-type    UAGGCUAAAUUUCCCUUUCCUAUUCCCUUUGUUUGCUUGUAAAUAUGAUUAAUUCCUGC
                □□□□□ ...                              □□□□□
pP16-pY      UAGGCUAAAUUUCCCUUUCCUAUUCCCUUUGUUUGCUUGUAAAUAUGAUUCCUGC
pP35-pY      UAGGCUAAAUUUCCCUUUCCUUUCCAAUUCC----UUUUGCUUGUAAAUAUGAUUCCUGC pΔ99-115     UAGGCUAAA----------------CCCUUUCCUAUUCCCUUUGUUUGCUUGUAAAUAUGAUUCCUGC
pΔ99-130     UAGGCUAAA-------------------------UUUGUUUUGCUUGUAAAUAUGAUUCCUGC
pΔ99-134     UAGGCUAAA-----------------------------UUUUGCUUGUAAAUAUGAUUCCUGC
pΔ96-134     UAGGCU--------------------------------UUUUGCUUGUAAAUAUGAUUCCUGC
pΔ93-134     UAG-----------------------------------UUUUGCUUGUAAAUAUGAUUCCUGC pΔ96-137     UAGGCU-----------------------------------UGCUUGUAAAUAUGAUUCCUGC
pΔ96-139     UAGGCU-------------------------------------CUUGUAAAUAUGAUUCCUGC
pΔ96-140     UAGGCU--------------------------------------UUGUAAAUAUGAUUCCUGC
pΔ96-141     UAGGCU---------------------------------------UGUAAAUAUGAUUCCUGC
pΔ99-144     UAGGCUAAA-----------------------------------------AAAUAUGAUUCCUGC
pΔ116-144    UAGGCUAAAUUUCCCUUU--------------------------------AAAUAUGAUUCCUGC
pΔ31-144     UAGGCUAAAUUUCCCUUUCCUAUUCCC-----------------------AAAUAUGAUUCCUGC
                                                                     ^^^^
                                                                      ts
```

FIG. 1.

```
          90        100       110       120       130       140       150
          |         |         |         |         |         |         |
HM175     UAGGCUAAAUUUCCC--UUUCCCUUUUCCCUUUCCU--A-UUCCUUUGUUUUGCUUGUAAAUAUUAAUU
AZ79      UAGGCUAAA-UUUCCC--UUUCCC-UGUCC---UUCCCUAUUUCCC-UUUGUUUUGCUUGUAUAUAUUAAUU
Chi81     UAGGCUAAA-UUUCCC--UUUCCC-UGUCC---UUCCCUAUUUCCC-UUUGUUUUGCUUGUAAAUAUUAAUU
Ita85     UAGGCUAAA-UUUCCC--UUUCCC-UGUCC---UUCCCUAUUUCCC-UUUGUUUUGCUUGUAAAUAUUAAUU
Ga88      UAGGCUAAA-UUUCCC--UUUCCC-UGUCC---UUCCCUAUUUCCCU-AUUUGUAUUGCUUGUAAAUAUUAAUU
CP*       UAGGCUAAA-UUUCCC--UUUCCC-UGUCC---UUCCCUAUUUACCUUUGUUUUGCUUGUAAAUAUUAAUU
HAS15     UAGGCUAAA-UUUCCC--UUUCCC-UGUCC---UUCCCU-AUUUCCUUUAUUU-GCUUGUAAAUAUUAAUU
LA*       UAGGCUAAA-UUUCCC--UUUCCC-UGUCC---UCCCUAUUUCCC-UUUGUUUUGCUUGUAAAUAUGAUU
MBB*      UAGGCUAAAUUUUCCC--UUUCCCCUUUUCC-UUUCCCCCUUCC--------------UUGUUUUGAUGUAAAUAUUAAUU
Ken       UAGGCUAA--UUUCCCCUUUUUCC--UUCCCUUUUCC-UUUCC----------------UUUA--UUG-UUGUAAAUAUUAAUU
CF53*     UAGGCUA--UUUCUCCC--UUCCCUUUUCC-UUUCC-------------------UGUUUUG--UGUAAAUAUUAAUU
KRM003*   UAGGCUAA--UUUCCC--UUUCC-UUUUCC-UUUCC-------------------UGUGUUA-UGUAAAUAUUAAUU
PA21*     UAGGCUAAA-UUUCCC--UUUCC--UUUCC-UUUCC-------------------UUUA-A-UG-UUGUAAAUAUGAUU
```

FIG. 4.

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:1:

TTTGCCTAGG CTATAGGCTC CATT                                  24

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:2:

TGAACCTGCA GGAACCAATA TTTA                                  24

(2) INFORMATION FOR SEQ ID NO:3:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:3:

TAAAAAATAT TGAT                                                      14

(2) INFORMATION FOR SEQ ID NO:4:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:4:

ATCAATATTT TTTA                                                      14

(2) INFORMATION FOR SEQ ID NO:5:

(i) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO:5:

GCCTATAGCC TAGGCAAACG                    20

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO:6:

AGAGAAACAG ATTTAAGAAC                    20

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO:7:

GCCAGAGCCT AGGGCAAGGG                    20

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO:8:

GTGACGTTCC AAACATCTGT                    20

(2) INFORMATION FOR SEQ ID NO:9:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO:9:

```
GGGGAGAGCC CTGG                                                                14
```

(2) INFORMATION FOR SEQ ID NO:10:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:10:

```
UAGGCUAAAU UUUCCCUUUC CCUUUUCCCU UUCCUAUUCC CUUUGUUUUG CUUGUAAAUA         60

UUAAUUCCUG C                                                              71
```

(2) INFORMATION FOR SEQ ID NO:11:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:11:

```
UAGGCUAAAU UUUCCCUUUC CCUUUUCCCU UUCCUAUUCC CUUUGUUUUG CUUGUAAAUA         60

UUGAUUCCUG C                                                              71
```

(2) INFORMATION FOR SEQ ID NO:12:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:12:

```
UAGGCUAAAU UUUCCCUUUC CCUUUUCCCU UUCCAAUUCC CUUUUGCUUG UAAAUAUUGA         60

UUCCUGC                                                                   67
```

(2) INFORMATION FOR SEQ ID NO:13:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:13:

```
UAGGCUAAAC CCUUUCCUAU UCCCUUUGUU UUGCUUGUAA AUAUUGAUUC CUGC               54
```

(2) INFORMATION FOR SEQ ID NO:14:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (xi) SEQUENCE DESCRIPTION: SEQ ID NO:14:

UAGGCUAAAU UUGUUUUGCU UGUAAAUAUU GAUUCCUGC                        39

(2) INFORMATION FOR SEQ ID NO:15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:15:

UAGGCUAAAU UUUGCUUGUA AAUAUUGAUU CCUGC                            35

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:16:

UAGGCUUUUU GCUUGUAAAU AUUGAUUCCU GC                               32

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:17:

UAGUUUUGCU UGUAAAUAUU GAUUCCUGC                                   29

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:18:

UAGGCUUGCU UGUAAAUAUU GAUUCCUGC                                29

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:19:

UAGGCUCUUG UAAAUAUUGA UUCCUGC                                  27

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:20:

UAGGCUUUGU AAAUAUUGAU UCCUGC                                   26

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:21:

UAGGCUUGUA AAUAUUGAUU CCUGC                                    25

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:22:

UAGGCUAAAA AAUAUUGAUU CCUGC                                    25

(2) INFORMATION FOR SEQ ID NO:23:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:23:

UAGGCUAAAU UUUCCCUUUC CCUUUAAAUA UUGAUUCCUG C                41

(2) INFORMATION FOR SEQ ID NO:24:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:24:

UAGGCUAAAU UUUCCCUUUC CCUUUUCCCU UUCCUAUUCC CAAAUAUUGA UUCCUGC    57

(2) INFORMATION FOR SEQ ID NO:25:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:25:

UAGGCUAAAU UUUCCCUUUC CCUUUUCCCU UUCCUAUUCC CUUUGUUUUG CUUGUAAAUA    60

UUAAUU                                                              66

(2) INFORMATION FOR SEQ ID NO:26:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:26:

UAGGCUAAAU UUCCCUUUCC CUGUCCUUCC CCUAUUUCCC UUUGUUUUGC UUGUAUAUAU    60

UAAUU                                                               65

(2) INFORMATION FOR SEQ ID NO:27:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:27:

```
UAGGCUAAAU UUCCCUUUCC CUGUCCUUCC CCUAUUUCCC UUUGUUUUGU UUGUAAAUAU    60

UAAUU                                                                65

(2) INFORMATION FOR SEQ ID NO:28:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:28:

UAGGCUAAAU UUCCCUUUCC CUGUCCCUUC CCUAUUUCCC UUGUUUUAUU UGUAAAUAUU    60

AAUU                                                                 64

(2) INFORMATION FOR SEQ ID NO:29:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:29:

UAGGCUAAAU UUCCCUUUCC CUGUCCUUCC CCUAUUUACC UUUGUUUUGC UUGUAUAUAU    60

UAAUU                                                                65

(2) INFORMATION FOR SEQ ID NO:30:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:30:

UAGGCUAAAU UUCCCUUUCC CUGUCCCUUC CCUAUUUCCC UUUAUUUGCU UGUAAAUAUU    60

AAUU                                                                 64

(2) INFORMATION FOR SEQ ID NO:31:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:31:

UAGGCUAAAU UUCCCUUUCC CUGUCCUUCC CUUAUUUCCC UUUGUUUUGC UUGUAAAUAU    60

UGAUU                                                                65
```

(2) INFORMATION FOR SEQ ID NO:32:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:32:

UAGGCUAAAU UUCCCUUUCC CUGUCCCUCC CUUAUUUCCC UUUGUUUUGC UUGUAAAUAU     60

UAAUU     65

(2) INFORMATION FOR SEQ ID NO:33:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:33:

UAGGCUAAAU UUUCCCUUUC CCCUUCCCCU UCCUUGUUUU GAUUGUAAAU AUUAAUU     57

(2) INFORMATION FOR SEQ ID NO:34:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:34:

UAGGCUAAAU UUCCCUUUUU CCCUUUCCCU UUAUUGUUGU AAAUAUUAAU U     51

(2) INFORMATION FOR SEQ ID NO:35:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (xi) SEQUENCE DESCRIPTION: SEQ ID NO:35:

UAGGCUAUUU CUCCCCUUCC CUUUUCCCUG UUUUGUGUAA AUAUUAAUU     49

(2) INFORMATION FOR SEQ ID NO:36:

(i) SEQUENCE CHARACTERISTICS:
        (A) LENGTH: 50 base pairs
        (B) TYPE: nucleic acid
        (C) STRANDEDNESS: single
        (D) TOPOLOGY: linear

```
        (ii) MOLECULE TYPE: cDNA to mRNA (iii) HYPOTHETICAL: NO (xi) SEQUENCE DESCRIPTION: SEQ ID NO:36:

UAGGCUAAUU UUCCCUUUUC CUUUUCCCUG UGUUAUUGUA AAUAUUAAUU             50

(2) INFORMATION FOR SEQ ID NO:37:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (xi) SEQUENCE DESCRIPTION: SEQ ID NO:37:

UAGGCUAAAU UUCCCUUUUC CCUUUCCCUU UAAUGUUGUA AAUAUUGAUU             50
```

HEPATITIS A VIRUS DELETION MUTANTS AND VACCINE FORMULATIONS CONTAINING THE SAME

This application is a continuation of prior application Ser. No. 08/273,594, filed Jul. 11, 1994, now U.S. Pat. No. 5,766,906.

This invention was made with government support under grants RO1-AI32599 and T32-AI07001 from the U.S. Public Health Service, and by grant DAMD 17-89-Z-9022 from the U.S. Army Medical Research and Development Command. The government has certain rights to this invention.

FIELD OF THE INVENTION

The present invention relates to hepatitis A virus containing deletion mutations in the 5' nontranslated region thereof, and live attenuated vaccine formulations containing the same.

BACKGROUND OF THE INVENTION

Like other members of the picornavirus family, hepatitis A virus (HAV, genus hepatovirus) contains a single-stranded, positive-sense RNA genome with a lengthy (735 nucleotide [nt]) 5' nontranslated region (5'NTR). The 5'NTR of HAV (HM175 strain) contains an internal ribosomal entry site (IRES) located between nt 152 and nt 735, which regulates cap-independent, internal initiation of translation of the viral polyprotein, although the level of efficiency with which the HAV IRES promotes translation is much less than that of other picornavirus IRES elements both in vivo and in vitro (E. Brown, A. Zajac, and S. Lemon, *J. Virol.* 68:1066–1074 (1994), L. Whetter, et al., *J. Virol.* In press (1994)). The 5'NTR of HAV may possibly have other functions which are essential for virus replication, including control of positive-strand RNA synthesis and possibly encapsidation (R. Andino et al., *Cell* 63:369–380 (1990)).

Although there are substantial differences between the predicted secondary structures of the 5'NTRs of HAV and all other picornaviruses, the secondary structure of the HAV 5'NTR more closely resembles that of the cardioviruses and aphthoviruses than the corresponding structure in rhinoviruses and most enteroviruses (E. Brown, et al., *J. Virol.* 65:5828–5838 (1991)). Among other similarities, the 5'NTRs of hepatoviruses, cardioviruses, and aphthoviruses share the potential to form two or more pseudoknots in the noncoding region upstream of the IRES element (E. Brown, et al., *J. Virol.* 65:5828–5838 (1991), E. Brown, A. Zajac, and S. Lemon, *J. Virol.* 68:1066–1074 (1994), B. Clarke, et al., *Nucleic Acids Res.* 15:7066–7079 (1987), S. Jang, et al., *J. Virol.* 63:1651–1660 (1989), R. Kuhn, N. Luz, and E. Beck, *J. Virol.* 64:4625–4631 (1990), C. Pleij, *Proc. VIII Int. Congr. Virol.* 49–50 (1990)). Also present in this region is a pyrimidine-rich sequence which consists of an almost pure polycytidylic acid tract in the cardioviruses and aphthoviruses. In the hepatoviruses, the corresponding region contains a mixture of uridylic acids and cytidylic acids (in a 24:14 ratio in the HM175 strain of HAV), with only two purines located within a 40-nt-long, nearly pure polypyrimidine tract (pY1 domain, nt 99 to 138). In each of these virus genera, this pyrimidine-rich tract appears to separate two discrete regions of RNA secondary structure (E. Brown, et al., *J. Virol.* 65:5828–5838 (1991), B. Clarke, et al., *Nucleic Acids Res.* 15:7066–7079 (1987)). A similarly located pyrimidine-rich tract is not found in either the enterovirus or rhinovirus 5'NTR.

There are other pyrimidine-rich tracts within the 5'NTR of HAV (K. Chang, E. Brown, and S. Lemon, *J. Virol.* 67:6716–6725 (1993)), but the pY1 domain is the lengthiest and most prominent of these regions. Although considerable sequence heterogeneity exists within this domain among different human hepatoviruses (E. Brown, et al., *J. Virol.* 65:5828–5838 (1991)), the general features of this domain are conserved among all strains of HAV. A striking aspect of the pY1 domain, which is unique to the HAV 5'NTR among all other picornaviral 5'NTRs, is the presence of tandem repeats of the sequence motif (U)UUCC(C). Curiously, this motif closely resembles the core sequence of the "box A" motif of Pilipenko et al. (E. Pilipenko, et al., *Cell* 68:119–131 (1992)), which is present in a conserved location in all picornaviruses, about 20–25 nt upstream of the initiator AUG and which may play an important role in internal initiation of translation.

Previous modeling of the secondary structure of the 5'NTR of HM175 virus predicted that the pY1 domain and the immediately adjacent sequence from nt 139 to nt 154 were likely to be single-stranded (E. Brown, et al., *J. Virol.* 65:5828–5838 (1991)).

SUMMARY OF THE INVENTION

Here, we present the results of RNase mapping of the secondary structure of the pY1 region of the HM175 5'NTR, and describe a series of mutant viruses with large deletions involving the pY1 domain. We show that the pY1 domain forms an ordered structural element downstream of the putative 5' pseudoknots of HAV, but that this ordered structure is not required for efficient replication in cultured cells as long as the sequence between nt 140 and nt 144 is present. In contrast, an extended single-stranded region immediately downstream of the pY1 domain, which includes nt 140 to nt 144, is required for efficient replication of the virus at physiologic temperatures.

Further disclosed herein is the attenuating nature of the foregoing mutations and their use in the preparation of live hepatitis A virus vaccines.

A first aspect of the present invention is a live hepatitis A virus deletion mutant having a deletion mutation in the 5' nontranslated region of the viral genome. The deletion mutation may be selected from the group consisting of (a) pY1 deletion mutations that cause the virus to retain the ability to replicate in monkey kidney cells; and (b) deletion mutations between nucleotides 140 and 144 that render the virus temperature sensitive. Advantageously, the deletion mutation may be an attenuating mutation. Examples include (i) the deletion of at least 6 nucleotides between nucleotide 94 and nucleotide 140, inclusive (e.g., deletion mutations such that the pY1 region of the viral genome is not more than 20 nucleotides in length), and (ii) the deletion of at least one nucleotide between nucleotides 141 and 144, inclusive.

A second aspect of the present invention is a cDNA encoding a virus as given above.

A third aspect of the present invention is a method for inducing protective immunity against hepatitis A virus. The method comprises administering to a subject an infectious, immunogenic, hepatitis A virus carrying an attenuating mutation as given above, the virus being administered in an amount effective to induce protective immunity against hepatitis A virus. Preferably, administration is by oral administration.

A fourth aspect of the present invention is the use of an infectious, immunogenic, hepatitis A virus as given above for the preparation of a medicament for imparting protective immunity against hepatitis A virus to a subject.

A fifth aspect of the present invention is a vaccine formulation useful for inducing protective immunity against hepatitis A virus, comprising, an infectious, immunogenic, hepatitis A virus carrying an attenuating mutation, as given above, in a pharmaceutically acceptable carrier.

The foregoing and other objects and aspects of the present invention are explained in detail in the drawings herein and the specification set forth below.

BRIEF DESCRIPTION OF THE DRAWINGS

FIG. 1 shows pY1 deletion mutations constructed within a full-length cDNA clone of the HM175 virus. The wild-type virus sequence is shown at the top, with mutant plasmids listed at the left. Boxes represent nucleotides predicted to be involved in base-pairing interactions in stem-loops IIb (nt 90 to 94) or IIIa (nt 155 to 159); Dots represent positions cleaved by single-strand specific RNases. Direct transfection results at 31° C. and 37° C. are shown at the right: (+) replication foci demonstrated; (−) no replication foci demonstrated; n.d., not determined. Nucleotides 140 to 144 which are deleted in ts viruses are indicated at the bottom.

FIG. 4 shows the alignment of 13 human hepatitis A virus strains between nt 90 and nt 155 (HM175/wt sequence numbering). Strains marked by (*) were sequenced after passage in cell culture, while others were sequenced directly from primate materials. Nucleotides flanking the region of interest which are conserved among all strains are shown in boldface type. Cytidylic acid residues within the (U)UUCC (C) motifs are indicated by a double underline. The precise origin of PA21 virus is obscure: this virus was isolated from a naturally infected captive owl monkey, but viruses with very similar nucleotide sequences have been recovered from humans (R. Jansen, G. Siegl, and S. Lemon, *Proc. Natl. Acad. Sci. USA* 87:2867–2871 (1990)). The sequence of Ken virus was determined from virus which had been passaged once in chimpanzees. Sequences of AZ79, Chi81, Ita85, Ga88, and Ken were provided by Dr. B. Robertson, Centers for Disease Control and Prevention, Atlanta. The sequence from strain CP was determined during the course of this work. For other sequences, see (E. Brown, et al., *J. Virol.* 65:5828–5838 (1991)).

DETAILED DESCRIPTION OF THE INVENTION

Figure 2C:
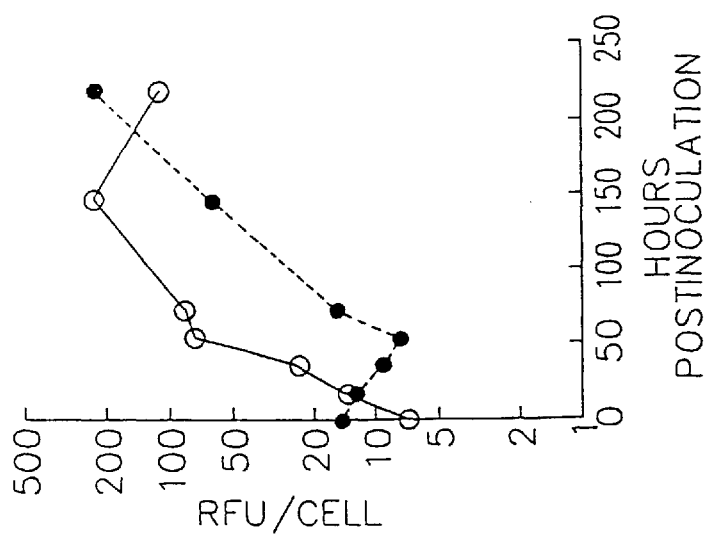
FIG. 2C shows intracellular virus accumulation under one step growth conditions at 31° C. or 37° C. for 131–144 virus. Conditions are the same as for FIG. 2A.

The numbering of nucleotides herein is given with reference to hepatitis A virus strain HM175. However, the instant invention is applicable to any hepatitis A virus strain. Numbering of nucleotides in strains of hepatitis A virus other than strain HM175 is accordingly carried out by alignment of other strains to HM175 for maximum homology within the regions flanking the pY1 region in the 5' and the 3' direction, and then applying the numbering system for strain HM175 to these other strains within the pY1 region. Since some hepatitis A virus strains contain pY1 regions shorter than HM175, pY1 regions missing or nut present under this numbering system are considered to be deleted. An example of such an alignment and numbering is shown in FIG. 4 (discussed below).

Viruses used to carry out the present invention for the purpose of making vaccine formulations, immunizing subjects, or making antibodies are live viruses that are immunogenic (i.e., produce an immune response to hepatitis A virus in a subject). The viruses may be viruses that are virulent but for the presence of the attenuating mutations described herein (the term "virulent" meaning capable of causing disease in an infected subject). Illustrative strains of hepatitis A virus used to carry out the present invention include, but are not limited to, strain HM175, strain CR326, strain MBB, strain GBM, etc.

Attenuating mutations to the pY1 region are preferably between nucleotides 94 and nucleotide 140 (since the pY1 region begins at nucleotide 99 and ends at nucleotide 138, it will be appreciated that the deletion may begin 5' to the pY1 region and end 3' to the pY1 region). The attenuating mutation is preferably at least 6 nucleotides in length (i.e., at least 6 are deleted), and may be 8, 10, 12, 14, 16, 18, 20, 22, 24, 26, nucleotides in length or more, up to deletion of the entire pY1 region. Larger deletions are preferred. Stated otherwise, viruses containing attenuating mutations of the instant invention have a pY1 region of not more than 20, 18, 16, 14, 12, 10, 8, 6, 4, or 2 nucleotides in length, total, up to the complete deletion (i.e. complete absence) of the pY1 region. Examples of hepatitis A viruses containing such deletion mutations are:

(a) Δ99–115 deletion mutants;
(b) Δ99–130 deletion mutants;
(c) Δ99–134 deletion mutants;
(d) Δ96–134 deletion mutants;
(e) Δ96–137 deletion mutants;
(f) Δ96–139 deletion mutants; and
(g) Δ96–140 deletion mutants.

The foregoing attenuating mutations may be combined with other attenuating mutations, such as deletion mutations to the 3' flanking region, as discussed below.

Attenuating mutations may also be in the 3' flanking region of the pY1 region (i.e., nucleotides 141–144 in the HM175 genome or other strains when numbered with reference to the HM175 genome; also sometimes designated nucleotides numbers 1–4 herein for convenience). Such attenuating mutations may be one, two, three, or four nucleotides in length. It is preferred that at least one, and more preferred that at least two, of nucleotides 142, 143, and 144 (or nucleotides 2, 3, and 4) be deleted. Most preferably at least all three of nucleotides 142 to 144 are deleted. Examples of hepatitis A viruses containing such deletion mutations are:

(h) Δ142 deletion mutants;
(i) Δ143 deletion mutants;
(j) Δ144 deletion mutants;
(k) Δ141–142 deletion mutants;
(l) Δ142–143 deletion mutants;
(m) Δ143–144 deletion mutants;
(n) Δ141–143 deletion mutants;

(o) Δ143–144 deletion mutants; and
(p) Δ140–144 deletion mutants.

The foregoing deletion mutations may be combined with other mutations (e.g., as all are in a Δ141–144 deletion mutant), including deletion mutations to the pY1 region as discussed above and below.

Attenuating mutations may be in both the pY1 region and the 3' flanking region thereof, in combination. Where the attenuating mutation is in both regions, the attenuating mutation may be either continuous or discontinuous. An example of a discontinuous attenuating mutation would be a deletion of all but 10 nucleotides of the pY1 region and the deletion of all but nucleotide 141 of the 3' flanking region. Examples of hepatitis A viruses containing such deletion mutations as continuous mutations are:

(q) Δ96–141 deletion mutants;
(r) Δ99–144 deletion mutants;
(s) Δ116–144 deletion mutants; and
(t) Δ131–144 deletion mutants.

The foregoing deletion mutations may optionally be combined with one or more other mutation(s), including other attenuating mutations, and/or other mutations that promote growth in cultured mammalian cells, elsewhere in the viral genome. Other such mutations are not critical so long as the virus is live, infectious and immunogenic. Examples of such other mutations include, but are not limited to, those described in U.S. Pat. No. 4,894,228 to Purcell et al. (the disclosure of all patent references cited herein is to be incorporated herein by reference). In addition, minor substitutions mutations may also be made within or adjacent to the deletion mutations herein described, as will be appreciated by those skilled in the art.

Attenuating mutations of the instant invention are introduced into cDNAs encoding live, infectious, hepatitis A virus by any suitable means, such as by PCR mutagenesis (discussed below) and by site-directed mutagenesis (see, e.g., U.S. Pat. No. 4,873,192 to Kunkel).

Virus carrying mutations of the present invention are made by conventional means. In general, a cDNA encoding live virus carrying the desired attenuating mutation is introduced into a cell line and the cell line cultured to produce live virus in the culture. Where the virus is to be used as a vaccine, the cell line is typically a continuous mammalian cell line that is certified for use in the production of human or veterinary vaccines (e.g., MMC5 cells, VERO cells, etc.). Once live virus containing the attenuating mutation is obtained, a seed stock of the RNA virus can be established and infected cells used to initiate new cultures without the need for introducing a cDNA into the cells. In the manufacture of a pharmaceutical formulation, virus is collected from the culture and combined with a pharmaceutically acceptable carrier, as discussed in greater detail below.

Oral vaccine formulations may be made from a culture of cells producing live virus containing the desired deletions in accordance with known techniques. The culture itself may be administered to the subject; the culture may be optionally filtered and/or clarified; stabilizers such as sucrose, $MgCl_2$, etc. may be added to the media.

Exemplary pharmaceutically acceptable carriers include, but are not limited to, sterile pyrogen-free water and sterile pyrogen-free physiological saline solution. Pharmaceutically acceptable carriers for oral administration may be a syrup, elixir, lozenge, etc. The vaccine formulation may be prepared in accordance with known techniques, such as illustrated by R. Purcell et al., *Vaccine Against Hepatitis A Virus*, U.S. Pat. No. 4,894,228.

Subjects which may be administered the live attenuated viruses and vaccine formulations disclosed herein include both human subjects and animal subjects (e.g., the veterinary treatment of primates such as owl monkeys, marmosets and chimpanzees).

Vaccine formulations of the present invention comprise an immunogenic amount of a live attenuated virus as disclosed herein in combination with a pharmaceutically acceptable carrier. An "immunogenic amount" is an amount of the attenuated virus sufficient to evoke an immune response in the subject to which the virus is administered. The particular dose employed is not critical, and depends upon the type and condition of the subject, the route of administration, etc. An amount of from about $10^4$ to $10^7$ radioimmunofocus forming units of the live virus per dose is typically suitable (titration of radioimmunofocus forming units is as described in S. Lemon et al., *J. Clin. Microbiol.* 17, 834–839 (1983).

Administration of the live attenuated viruses disclosed herein may be carried out by any suitable means, including both parenteral injection (such as intraperitoneal, subcutaneous, or intramuscular injection), by oral administration, and by topical application of the virus (typically carried in the pharmaceutical formulation) to an airway surface. Topical application of the virus to an airway surface can be carried out by intranasal administration (e.g., by use of a dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed. See, e.g., U.S. Pat. No. 5,304,125 to D. Leith; U.S. Pat. No. 5,299,566 to C. Davis and R. Snyder; U.S. Pat. No. 5,290,550 to R. Fisher and W. Metzger; and U.S. Pat. No. 5,292,498 to R. Boucher.

While the viruses, methods and formulations of the present invention have been described above with reference to producing protective immunity, they may also be used to simply produce antibodies in animals, which antibodies may be used for the purpose of detecting and diagnosing hepatitis A virus in accordance with conventional diagnostic techniques.

The present invention is explained in greater detail in the examples set forth in the following experimental section.

Experimental

I. MATERIALS AND METHODS

Cells. HAV was propagated in continuous African green monkey kidney (BS-C-1) or fetal rhesus kidney (FRhK-4) cells as previously described (L. Binn, et al., *J. Clin. Microbiol.* 20:28–33 (1984)).

HAV cDNA plasmids. Deletion mutations were constructed within an infectious, full length cDNA clone of the HM175 strain of HAV (FIG. 1). The parental clone was a chimeric infectious cDNA, pG7/18fP2, which was constructed by replacing the small SacI/EcoRI fragment of pG3/HAV7 (J. Cohen, et al., *J. Virol.* 61:3035–3039 (1987), S. Day, et al., *J. Virol.* 66:6533–6540 (1992)) (HM175/P35 virus sequence) with the corresponding cDNA fragment from a rapidly replicating, cytolytic variant (HM175/18f virus) (S. Lemon, et al., *J. Virol.* 65:2056–2065 (1991)), essentially replacing the P2 region of HM175/P35 with that of HM175/18f virus (S. Lemon, et al., *J. Virol.* 65:2056–2065 (1991)). Transfections with pG7/18fP2 RNA give rise to visible, macroscopic replication foci in radioimmunofocus assays (S. Lemon, L. Binn, and R.

Marchwicki, *J. Clin. Microbiol.* 17:834–839 (1983)) within 7 to 10 days, while transfections with pG3/HAV7 RNA generally require 14 to 21 days. Because the 5'NTR of pG7/18fP2 is derived from HM175/P35 virus (J. Cohen, et al., *Proc. Natl. Acad. Sci. USA* 84:2497–2501 (1987)), we refer to this plasmid as pP35-pY1 in this communication. Compared with the wild type sequence, pP35-pY1 contains a 4-nt deletion (nt 131 to 134) and a single point mutation (nt 124, U to C) within the pY1 domain (J. Cohen, et al., *Proc. Natl. Acad. Sci. USA* 84:2497–2501 (1987)). For consistency, all nucleotide numbering is according to the wild-type HM175 virus sequence (J. Cohen, et al., *J. Virol.* 61:50–59 (1987)). Except where noted, manipulations of the pY1 domain were carried out in pB1.0, which contains a cDNA copy of the first 2024 bases of the HM175/P16 (rather than HM175/P35) virus sequence (E. Brown, A. Zajac, and S. Lemon, *J. Virol.* 68:1066–1074 (1994), R. Jansen, J. Newbold, and S. Lemon, *Virology* 163:299–307 (1988)). The pY1 domain of HM175/P16 is identical to that of the wild type virus. Outside of the pY1 domain, the sequence of the P16 and P35 variants of HM175 differ at only a single base position in the region manipulated during mutagenesis (nt 25 to 632, see below). We have shown previously that these two 5'NTR sequences are functionally identical with respect to their ability to support viral replication in cultured cells (S. Day, et al., *J. Virol.* 66:6533–6540 (1992)).

Several different mutagenesis strategies were employed in constructing the deletion mutants shown in FIG. 1. The initial strategy involved construction of a subclone with unique restriction sites flanking the pY1 domain. Mutagenic oligonucleotide primers (TTTGCCTAGGCTATAGGCT CCATT [positive sense]) and (TGAACCTGCAGGAA CCAATATTTA [negative sense]) were used to amplify the region between bases 78 and 168 of pB1.0 by polymerase chain reaction (PCR) and to create NlaIV sites immediately downstream of the second predicted pseudoknot of domain II (stem loop IIb, nt 95) and immediately upstream of the first predicted stem loop of domain III (IIIa, nt 154) (not shown) (E. Brown, et al., *J. Virol.* 65:5828–5838 (1991)). The resulting 90 base PCR product containing the NlaIV sites was gel-purified and used as the negative strand primer in a second PCR reaction, in which the positive strand primer began at the −7 position relative to the HAV sequence and included the HindIII site at which the HAV insert is cloned in the vector. The 0.17 kb product of the second PCR reaction was digested with HindIII and PstI, and then ligated with a PstI/BamHI fragment of pB1.0 (nt 162 to 632), into HindIII and BamHI sites of pGEM3zf(−) (Promega) to create pG3zNla. This clone contains the first 632 bases of the HM175/P16 sequence with new NlaIV sites at nt 95 and nt 154. Several clones with specific mutations within the pY1 domain were constructed by ligation of blunt-ended inserts into pG3zNla following digestion with NlaIV and removal of the region spanning nt 95 to 154. The three base changes which created the new NlaIV sites in PG3zNla were at positions 96, 97, and 153, and were thus removed prior to the ligations.

A mutant insert containing a 46-base deletion between nt 99 and nt 144 was created by annealing the two complementary oligonucleotides (TAAAAAATATTGAT [positive sense]) and (ATCAATATTTTTTA [negative sense]), and ligating the duplex into pG3zNla. The resulting subclone, containing the correct HAV sequence (HM 175/p16) from 0 to 632 except for the deletion, was used to create a full-length cDNA clone, pΔ99–144 (deletion spanning nt 99 to 144) (FIG. 1), by ligating the 0.61 kb BspEI/BamHI fragment (HAV sequence between bases 25 and 632) with the 9.7 kb fragment of pP35-pY1 resulting from BspEI and partial BamHI digestion. As a control for these manipulations, an insert which contained the sequence of HM175/p16 virus spanning nt 96 to 155 (HM175/P16 numbering) was created using pB1.0 as template in a PCR. This sequence was similarly introduced into pP35-pY1 to create pP16-pY1, which contains the HM175/P16 (or HM175/wt) sequence within the pY1 domain.

PCR mutagenesis was subsequently used to create a series of full-length cDNA clones with progressive deletions from the 5' or 3' end of the pyrimidine-rich tract. Fifty to 60 base long negative-sense primers containing the PstI site at nt 162 were used to add back either 14 or 17 bases of the deleted pyrimidine-rich sequence to the PCR template, pΔ99–144, which lacked the entire pY1 domain. The positive sense primer in each of these reactions spanned the BspEI site at nt 25. The resulting PCR products were digested with BspEI and PstI, and ligated into the unique BspEI/PstI site of a subclone containing the 0.63 kb HindIII/BamHI fragment of HAV (HM175/P16 sequence). Finally, a 0.61 kb product derived by digestion of this intermediate subclone with BspEI/BamHI was ligated with the 9.7 kb BspEI/BamHI fragment of pP35pY1, as above. Clones obtained in this manner included pΔ99–130 and pΔ116–144 (FIG. 1). A similar strategy, using pΔ99–130 and pΔ116–144 as templates for PCR mutagenesis, was taken to add back or delete additional nucleotides creating pΔ99–115, pΔ99–134 and pΔ131–144. dsDNA sequencing confirmed the fidelity of PCR amplified segments and the mutations present in individual cDNA clones.

Additional full-length mutant clones (pΔ96–134, pΔ93–134, pΔ96–137, pΔ96–139, pΔ96–140, and pΔ96–141) (FIG. 1) were created by heteroduplex site-directed mutagenesis (S. Inouye and M. Inouye, *Academic Press, Orlando* 181–206 (1987)), using pΔ99–134, pΔ96–134, or pΔ96–137 as templates, without construction of the intermediate subclone. Template sequence between the BspEI site (nt 25) and the HpaI site (nt 353) was made single-stranded in heteroduplexes formed by DNA which had been digested with BglI (first strand) or BspEI/HpaI (second strand). A mutagenic oligonucleotide primer was annealed to this region, the single-stranded regions of the heteroduplexes were filled in by the Klenow fragment of DNA polymerase I, and the ends ligated by T4 DNA ligase. All cDNA clones made by heteroduplex site-directed mutagenesis were sequenced between the BspEI and HpaI sites.

Physical mapping of RNA secondary structure. RNAs representing the first 1 kb of the HAV genome were synthesized as runoff transcripts from DNA clones linearized at the XmnI site (nt 980) or the NdeI site (nt 1108). Reaction products were digested with DNAse, extracted with phenol-chloroform, and ethanol precipitated. The RNA transcripts were heated to 65° C. for 3 minutes and allowed to cool slowly to 4° C. in the presence of 10 mM $MgCl_2$-10 mM Tris (pH 7.6, or at lower pH where indicated).

Enzymatic modification of 3 μg RNA by RNase T1 (Pharmacia), RNase T2 (BRL), RNase S1 (Pharmacia), or RNase V1 (Pharmacia) was carried out at room temperature in the presence of 20 μg of carrier tRNA and 10 mM $MgCl_2$, 10 mM Tris (and 1 mM $ZnSO_4$ for S1 Nuclease), at pH 7.6 (except where noted) in a total volume of 40 μL for 10 minutes. Optimal RNase concentrations were determined empirically for each batch of RNA. Reactions were stopped by the addition of excess tRNA. The modified RNA (including mock digested RNA not subjected to nucleases) was ethanol precipitated, and analyzed by primer extension using a [$^{32}$P]-labelled negative strand primer and 3 units of avian myeloblastosis virus reverse transcriptase (Life Sciences) at 42° C. (unless otherwise noted) for 30 minutes (E. Brown, et al., *J. Virol.* 65:5828–5838 (1991)). The primers used in these reactions included A-75 (GCCTATAGCCTAGGCAAACG), A-170 (AGAGAAACAGATTTAAGAAC), A-241 (GCCAGAGCCTAGGGCAAGGG), and A-324 (GTGACGTTCCAAACATCTGT). Reaction products were separated on a 6% polyacrylamide gel, in parallel with dideoxy sequencing reactions using unmodified RNA.

RNA transcription and transfection. Transcription reactions with SP6 RNA polymerase (Promega) were carried out in 20-µl reaction volumes, with 1.25 mM R130 nucleoside triphosphates and 1.5 µg of HaeII-digested DNA, for 90 minutes at 37° C. Immediately upon termination of the reaction, 18 µl of the reaction mix was mixed with 30 µl (30 µg) of Lipofectin (BRL), diluted to 100 µl according to the manufacturer's directions, and used to transfect one 60-mm petri dish culture of BS-C-1 or FRhK-4 cells. Visual inspection of transcription products in 0.1% sodium dodecyl sulfate (SDS) agarose gels indicated that the quantity of full length 7.5 kb RNA was approximately the same in each transfection. However, in one transfection, RNA products were labelled with trace amounts of $^{32}$P and the resulting 7.5 kb bands excised from the gel and counted in a scintillation counter. The amount of radioactivity in the 7.5 kb bands from different transcription reactions differed by less than 20% (results not shown), confirming the validity of the visual quantitation.

For transfections, cells were washed twice with serum-free medium, fed with 2.5 ml of serum-free medium and the RNA-Lipofectin mixture added dropwise. Following an overnight incubation, 5 ml of medium containing 10% fetal bovine serum were added to each culture. Except where noted, transfections were carried out as direct transfection/radioimmunofocus assays (S. Day, et al., *J. Virol.* 66:6533–6540 (1992), S. Lemon, L. Binn, and R. Marchwicki, *J. Clin. Microbiol.* 17:834–839 (1983)). Thus, twenty-four hours after the addition of serum-containing medium, the cells were overlaid with agarose. The cultures were incubated for 7–9 days at 31–32° C., 35.5° C., or 37° C., and processed for detection of radioimmunofoci as described previously (S. Lemon, L. Binn, and R. Marchwicki, *J. Clin. Microbiol.* 17:834–839 (1983)).

Where indicated, virus stocks were rescued from transfected FRhK-4 (or BS-C-1) cells maintained without agarose overlays. At harvest, cells were scraped into 4 ml of medium, and subjected to 3 freeze-thaw cycles followed by brief sonication. Cellular debris was removed by low speed centrifugation followed by chloroform extraction, and first passage virus stocks were stored at −70° C. Higher titer (second passage) master seed stocks were prepared by inoculating 900 cm$^2$ roller bottle cultures of confluent FRhK-4 cells with first-passage virus and harvesting as described above after 7 to 9 days of incubation at 35.5° C. (or 31° C. in the case of temperature-sensitive [ts] mutants). Working virus (third passage) stocks were recovered by similar passage of the master seed stock in BS-C-1 cells. Virus titers are reported as radioimmunofocus-forming units of virus (rfu) per milliliter (rfu/ml) (S. Lemon, L. Binn, and R. Marchwicki, *J. Clin. Microbiol.* 17:834–839 (1983)).

RNA sequencing. To confirm the presence of mutations in rescued viruses, the genomic RNA of working virus stocks was sequenced in the region of the pY1 domain after reverse transcription and amplification of cDNA (nt 31 to 317) by an antigen-capture-PCR method (R. Jansen, G. Siegl, and S. Lemon, *Proc. Natl. Acad. Sci. USA* 87:2867–2871 (1990)). The PCR product was gel-purified, and used as template in cycle sequencing reactions with ΔTaq DNA polymerase (U.S. Biochemical Corp.). A negative strand sequencing primer, SLA-229 (GGGGAGAGCCCTGG), was used in these reactions. The same strategy was used to sequence hepatitis A virus strain CP.

One-step growth curve analysis of rescued virus. Approximately 2×10$^5$ BSC-1 or FRhK-4 cells in individual, replicate wells of a 24-well culture plate were inoculated at a high multiplicity of infection (range, 2 to 5). At specified time points, supernatant fluids were removed from the cultures. The cells were washed twice and lysed by the addition of 1 ml 0.1% SDS as described previously (S. Day, et al., *J. Virol.* 66:6533–6540 (1992)). The viral titer of supernatant fluids or cell lysates was subsequently determined by radioimmunofocus assays carried out in BS-C-1 cells at 35.5° C. (or 31° C. for ts mutants).

Thermostability assay. Normal and ts virus stocks were diluted to 6.8 log$_{10}$ rfu/ml in cell culture medium containing 3% fetal bovine serum, divided into four aliquots, and placed at 0° C. Individual aliquots of each virus stock were heated to 50° C., 55° C., or 60° C. for 10 minutes in an automatic thermal cycler. The residual infectious virus titer was determined by radioimmunofocus assay of BS-C-1 cells at 31° C.

II. RESULTS

Secondary structure of the 5' 300 nt of the 5'NTR of HAV. Covariant nucleotide substitutions within the 5'NTRs of different strains of HAV predict double-stranded helices that are conserved in the secondary structure of the RNA (E. Brown, et al., *J. Virol.* 65:5828–5838 (1991)). The presence of numerous covariant substitutions provided a high level of confidence in predictions of the structure of the 3' half of the 5'NTR, but only a single cluster of covariant substitutions (near the top of stem-loop IIIa) (not shown) has been identified upstream of nt 330. Thus previous predictions of the structure in this region of the 5'NTR (E. Brown, et al., *J. Virol.* 65:5828–5838 (1991)) (not shown) were based almost entirely upon thermodynamic considerations. To test the validity of these predictions, we determined the sites at which synthetic 5'NTR RNA was susceptible to cleavage by RNases which preferentially cleave single-stranded (RNase S1, RNase T1, RNase T2) or double-stranded (RNase V1) RNA. The synthetic RNAs utilized in these experiments represented the 5' 980 or 1108 nucleotides of the HAV genome and included 10 additional nucleotides at the 5' terminus which were derived from the vector. These experiments generally confirmed the predicted secondary structure. Each region within the 5' 303 nts of the 5'NTR was examined in at least two separate experiments. The most prominent single-strand-specific RNAse cleavage sites were located precisely in the predicted loop regions of stem-loops I, IIa, IIb and IIIb, and at the 5' and 3' ends of the extended region flanking the pY1 domain (nt 96 to 98 and 135 to 152). The most prominent sites at which the double-strand-specific RNase V1 cleaved the RNA were located within the stems of stem-loops IIb (nt 81 to 84) and IIId (nt 282 to 285). Other V1 cleavage sites were at nt 74 to 76, in a region between stem-loops IIa and IIb which would be base paired in the second predicted pseudoknot (not shown).

Surprisingly, RNase V1 cleaved the RNA at multiple sites within the pY1 domain, despite previous predictions that this region should be single stranded. These V1 cleavage sites centered on five groups of cytidylic acids that occur as part of the repetitive (U)UUCC(C) motifs, but V1 cleavage also occurred at uridylic acids located just downstream of the pY1 domain (nt 141 and 142). Significantly, no single-strand-specific enzymes cleaved the RNA within the region containing the five repetitive (U)UUCC(C) motifs (nt 99 to 130), although relatively strong single-strand cleavage sites flanked this domain. These results indicate that the pY1 domain does not exist as a randomly ordered single-stranded RNA segment, but that it possesses an ordered structure. The V1 cleavages in this domain may reflect helical stacking of the RNA, or possibly noncanonical hemiprotonated C—C base pairing (K. Gehring, J. Leroy, and M. Gueron, *Nature* 363:561–565 (1993)) (see Discussion). Since hemiprotonated C—C base pairing is more likely to occur at acidic pH, we carried out V1 digestions over a pH range of between 7.6 and 6.0. There was no enhancement of V1 cleavage at low pH, as might be expected if C—C base pairing were occurring (data not shown). Parallel analysis of a different region of the 5'NTR confirmed that the enzyme was fully active at pH 6.0.

These experiments also provided indirect evidence for the existence of the two pseudoknots predicted to involve stem-loops IIa and IIb (not shown). Strong stops for reverse transcriptase were found to occur exactly at the 3' end of these predicted stem-loop structures-(not shown). A similar strong stop was not present at the 3' end of the 5' terminal hair-pin (stem-loop I), although a much weaker stop was sometimes observed within a G—C rich region of this stem-loop (nt 26 to 28), (not shown). Although it is possible that the helical stems of stem-loops IIa and IIb are sufficiently stable to inhibit the progression of reverse transcriptase, the fact that a similar strong stop was not observed at the 3' end of stem loop I, which is longer, more G—C rich, and predicted to have a much lower free energy (not shown) (A. Jacobson, et al., *Nucleic Acids Res.* 12:45–52 (1984)), suggests that stem loops IIa and IIb are further stabilized by their Involvement in pseudoknots.

Deletion mutagenesis of the pY1 domain. Although the sequence within the pY1 domain is more variable than that in any other region of the 5'NTR (E. Brown, et al., *J. Virol.* 65:5828–5838 (1991)), all human hepatovirus strains studied thus far contain a pyrimidine-rich sequence in this region which is 21 to 40 nt in length (see FIG. 4). Each of these virus strains also preserves the repetitive (U)UUCC(C) motif, although the number of these motifs varies from strain to strain. To determine whether deletion mutations within and flanking the pY1 tract would impair replication, we constructed a full-length cDNA clone with a large deletion (pΔ99–144) in this domain. This deletion mutant was subsequently used for construction of additional mutants with smaller deletions (FIG. 1) (see Materials and Methods). Each of the deletion mutations was confirmed by double-stranded DNA sequencing prior to RNA transcription and transfection into permissive BS-C-1 or FRhK-4 cells. Results of transfections at 35.5° C. or 31° C. are summarized in FIG. 1.

In direct transfection-radioimmunofocus assays carried out at 35.5° C., transfection of RNA derived from pP16-pY1, which contains the wild-type HM175 sequence in the pY1 domain, generated viral replication foci which were identical in size to those derived from RNA transcribed from the parental construct, pP35-pY1 (data not shown). However, multiple transfections with pΔ99–144 RNA at standard temperature conditions of 35.5° C., in either FRhK-4 or BS-C-1 cells and including two blind passages of transfected cell harvests, never resulted in recovery of viable virus (FIG. 1). pΔ99–144 DNA was sequenced completely within the manipulated region (nt 25 to 632). There were no changes from the parental sequence other than the expected 46-nt deletion. To determine whether a lethal mutation may have occurred elsewhere in the genome, the BspEI/BamHI fragment (nt 25 to 632) from pΔ99–144 was replaced with the corresponding fragment from the viable mutant pP16-pY1. As expected, RNA from the resulting clone generated replication foci that were identical in size to those of pP16-pY1. Thus, deletion of an extended sequence between stem-loops IIb and IIIa (Δ99–144, FIG. 1) resulted in the absence of successful RNA transfection at physiologic temperature.

Figure 3:
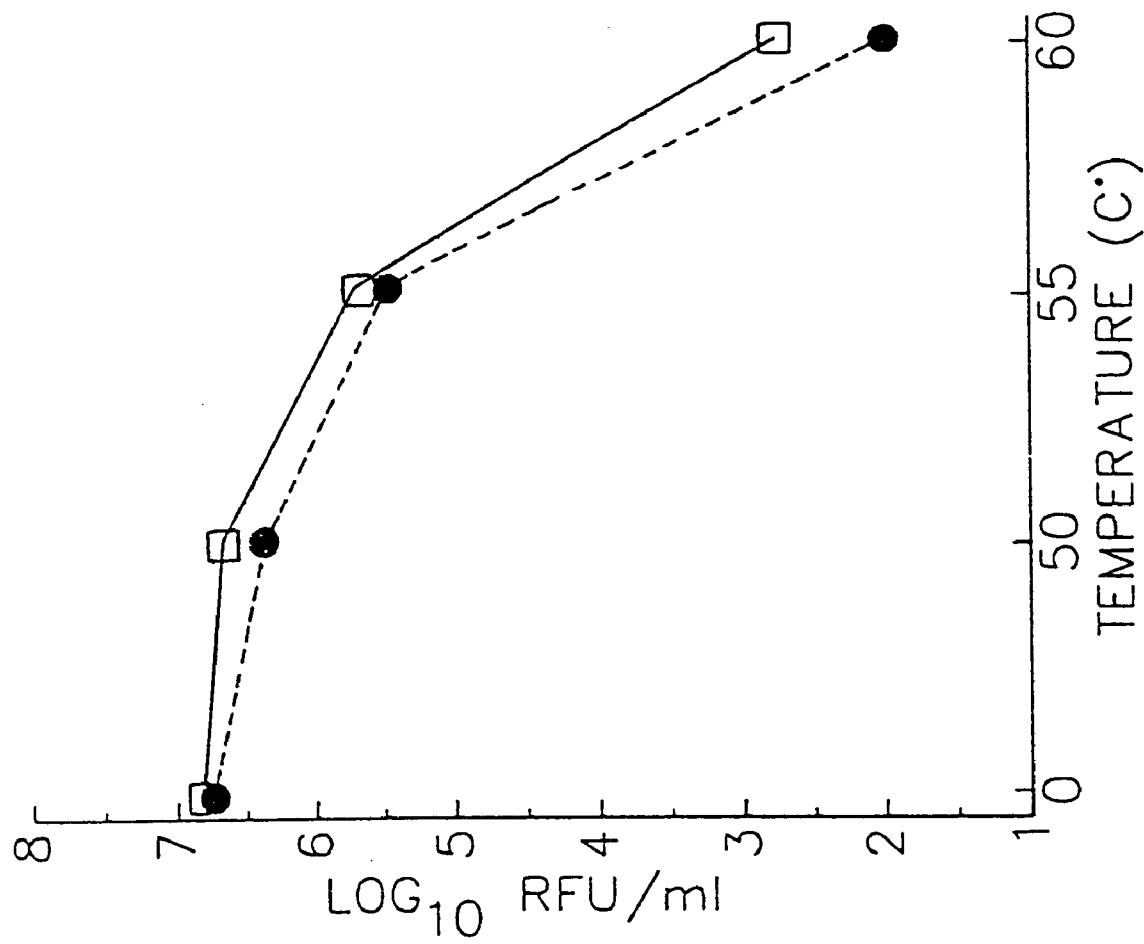
FIG. 3 shows the thermostability of the P16-pY1 (□) and ts Δ131–144 (●) viruses. Virus stocks were incubated at the indicated temperature for 10 minutes, and the surviving virus titer determined by radioimmunofocus assay of BS-C-1 cells at 31° C.

RNA derived from cDNA clones with smaller deletions in the pY1 domain proved to be infectious under these conditions (FIG. 3). However, two different replication phenotypes were observed among the rescued viruses (not shown). Viruses rescued from pΔ99–115, pΔ99–130, pΔ99–134, pΔ96–134, pΔ96–137, and pΔ96–139 produced replication foci which were similar in size to those of pP16-pY1. Thus, a 44-nt-long deletion mutation which included the entire pY1 domain (Δ96–139) resulted in no apparent impairment of virus replication. In contrast, virus rescued from pΔ131–144 produced very small replication foci in radioimmunofocus assays carried out at 35.5° C. The small replication focus size observed with this virus prompted an examination of its temperature sensitivity. Parallel titrations of Δ131–144 virus in BS-C-1 cells at 31° C. and 37° C. demonstrated a difference of 1.8 $\log_{10}$ rfu/ml in the titer of the working virus stock determined in radioimmunofocus assays carried out at these two temperatures (ts index), confirming that Δ131–144 virus had a temperature-sensitive (ts) replication phenotype (Table 1). In contrast, the ts index of P16-pY1 virus was 0.35±0.08 $\log_{10}$ rfu/ml in multiple assays. Consistent with these results, replication foci of Δ131–144 virus were nearly as large as those of P16-pY1 virus at 31° C. (data not shown).

ts Phenotypes of viruses with pY1 deletions extending to nt 140 to 144. Recognition of the ts phenotype of Δ131–144 virus led us to reevaluate the infectivity of RNA transcribed from pΔ99–144 and pΔ116–144, both of which failed to generate infectious virus in transfections of FRhK-4 or BS-C-1 cells at 35.5° C. (FIG. 1).

TABLE 1

TEMPERATURE SENSITIVITY OF 5'NTR DELETION MUTANTS

| Virus | Radioimmunofocus Size[1] | | ts index[2] | Sequencing[3] |
|---|---|---|---|---|
| | 31° C. | 37° C. | | |
| P16-pY1 | +++ | +++ | 0.35 ± 0.08 | Yes |
| P35-pY1 | +++ | +++ | 0.22 | Yes |
| 99-115 | +++ | +++ | 0.11 | Yes |
| 99-130 | +++ | +++ | 0.54 | Yes |
| 99-134 | +++ | +++ | 0.21 | Yes |
| 96-134 | +++ | +++ | n.d.[4] | Yes |
| 96-137 | +++ | +++ | 0.29 ± 0.04 | Yes |
| 96-139 | +++ | +++ | 0.40 | n.d. |
| 96-140 | ++(+) | + | 0.73 ± 0.17 | n.d. |
| 96-141 | ++(+) | + | >1.40 | Yes |
| 99-144 | ++ | (+) | 3.60 | Yes |

TABLE 1-continued

TEMPERATURE SENSITIVITY OF 5'NTR DELETION MUTANTS

| Virus | Radioimmunofocus Size[1] | | ts index[2] | Sequencing[3] |
|---|---|---|---|---|
| | 31° C. | 37° C. | | |
| 116-144 | ++(+) | (+) | 1.90 | Yes |
| 131-144 | ++(+) | + | 1.80 | Yes |

[1]The relative sizes of replication foci were scored subjectively: +++, equivalent to parental P16-pY1 virus; ++(+), occasionally equivalent to P16-pY1 but tended to be smaller; ++, almost always smaller than P16-pY1; +, small foci but always apparent; (+), tiny foci not always apparent in radioimmunofocus assays.
[2]ts index = $\log_{10}$ [titer 31° C.] − $\log_{10}$ [titer 37° C.] in radioimmunofocus assays carried out in BS-C-1 cells, S.E. where 3 or more assays were carried out. The 96-139 result is a mean of two assays, and the 96-141 result a mean of 3 assays (see Results).
[3]Mutation confirmed by RNA sequencing of rescued virus.
[4]n.d. = not done.

Repeat RNA transfections of FRhK-4 cells at 31° C. resulted in the rescue of viruses with marked ts phenotypes (not shown). The ts index of Δ99–144 virus was 3.6 $\log_{10}$ rfu/ml, while that of Δ116–144 virus was 1.9 $\log_{10}$ rfu/ml (Table 1). Because the ts indices of the Δ96–137 and Δ96–139 viruses were 0.29±0.04 and 0.40 $\log_{10}$ rfu/ml respectively, similar to that of the parent P16-pY1 virus (Table 1), these results suggested that the 3' extension of the deletion to include nt 140 to 144 was responsible for the ts replication phenotype. Interestingly, although deletion of the region spanning nt 99 to 130 (Δ99–130 and Δ99–134 viruses, Table 1) had no significant impact on virus replication at 37° C., the deletion of this region in association with the deletion of nt 131 to 144 resulted in a significant enhancement of the ts phenotype (compare the ts indices of the Δ99–144 and Δ131–144 viruses, 3.6 versus 1.8 $\log_{10}$ rfu/ml, respectively, Table 1). Because the ts index of the Δ116–144 virus was only 1.9, this enhancement of the ts phenotype was due primarily to deletion of the highly conserved first 2.5 (U)UUCC(C) motifs located between nt 99 and 115.

In order to define more precisely the nucleotide deletions responsible for the ts phenotype, two additional mutant cDNA clones were constructed, pΔ96–140 and pΔ96–141. RNA transfections at 35.5° C. produced viruses with moderate ts phenotypes. The ts index of Δ96–140 virus was 0.73±0.17 $\log_{10}$ rfu/ml, greater than that of the parent virus P16-pY1 (0.35±0.08 $\log_{10}$ rfu/ml) (Table 1). The ts index of Δ96–141 virus was >1.4 $\log_{10}$ rfu/ml (1.5, >1.12, and >1.5 $\log_{10}$ rfu/ml in three separate experiments). Thus, progressively greater ts indices were observed with viruses in which the pY1 deletion mutations extended in a 3' direction into the sequence spaning nt 140 to 144 (GUUGU). However, we do not yet know whether deletion of this sequence alone confers the ts phenotype. Although these ts viruses replicated much more efficiently at the permissive temperature, the replication foci of viruses with very large deletions (Δ96–141 and Δ99–144) were smaller than those of non-ts viruses (e.g. Δ96–137) at 31° C.

Double-stranded DNA sequencing of the cDNA region (nt 25 to 632) manipulated during mutagenesis of two of the ts cDNA clones (pΔ131–144 and pΔ116–144) documented only the expected deletion mutations. Replacement of this segment in the non-ts pP16-pY1 clone with the corresponding segment from pΔ131–144 conferred the ts phenotype on the product virus, confirming that the reduced replication capacity at 37° C. was due to the engineered deletion and not to an adventitious mutation elsewhere in the genome. Equally important, the expected deletions were confirmed in the RNA sequence of each of the rescued viruses (except Δ96–139 and Δ96–140, which were not sequenced) by antigen-capture-PCR of virus, followed by double-stranded DNA sequencing of the amplified product (Table 1). In no case was there reason to suspect that any of the rescued virus stocks had developed revertant or pseudorevertant mutations to compensate for the engineered deletions, since replication foci were numerous and similar in size on primary passage in direct transfection/radioimmunofocus assays.

The phenotype of individual mutants was the same following successful transfection of either BS-C-1 or FRhK-4 cells. BS-C-1 cells were consistently more difficult to transfect, but the replication foci of each of the rescued viruses was larger in BS-C-1 cells than in parallel transfections carried out in FRhK-4 cells (data not shown). This observation is consistent with the fact that each of these viruses contains cell-culture adaptation mutations at nt 152 and 203 to 204 which have been shown to promote replication of the virus in BS-C-1 but not FRhK-4 cells (S. Day, et al., J. Virol. 66:6533–6540 (1992)).

The phenotypes of the rescued viruses remained stable for up to four passages as judged by the size of replication foci in radioimmunofocus assays. Further evidence for the stability of the ts phenotype was provided by experiments in which BS-C-1 cells infected with ts variants (Δ99–144 and Δ96–141 virus) were maintained for up to 3 weeks at the nonpermissive temperature (37° C.), after an initial 24-hour incubation at the permissive temperature (31° C.). Virus harvests prepared from these cells were subsequently tested in radioimmunofocus assays at the nonpermissive temperature in order to detect large focus revertants. No such revertants were isolated (data not shown).

Figure 2B:
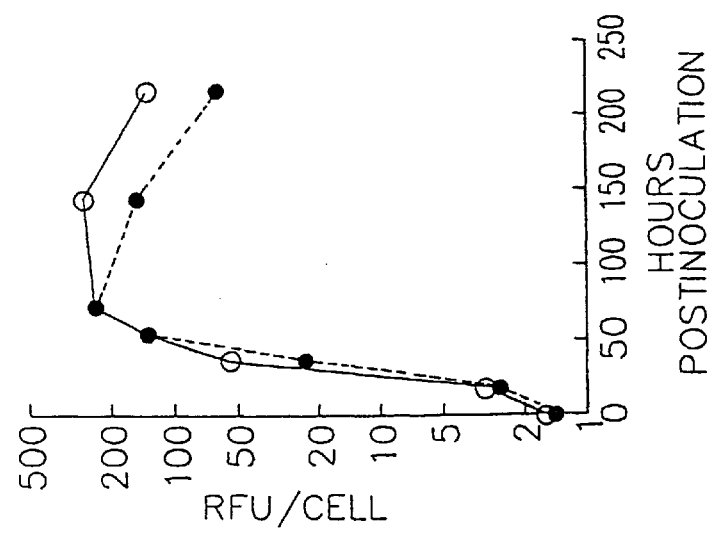
FIG. 2B shows intracellular virus accumulation under one step growth conditions at 31° C. or 37° C. for 96–137 virus. Conditions are the same as for FIG. 2A.
Figure 2A:
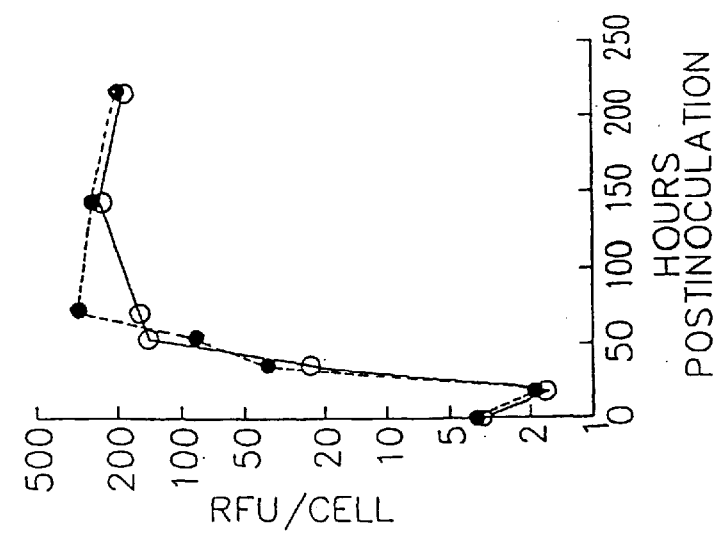
FIG. 2A shows intracellular virus accumulation under one step growth conditions at 31° C. or 37° C. for the P16-pY1 virus. BS-C-1 cells were infected with a virus inoculum calculated to provide a multiplicity of infection of approximately 3 infectious particles per cell and then incubated at either 31° C. (O) or 37° C. (■). At the indicated time points, monolayers were washed and lysed by the addition of 0.1% SDS. Virus titers in lysates were determined by radioimmunofocus assay in BS-C-1 cells at 31° C.

Analysis of ts virus replication under one-step growth conditions. Although radioimmunofocus size is an accurate measure of the replication efficiency of HAV in cultured cells (S. Day, et al., J. Virol. 66:6533–6540 (1992)), BS-C-1 and FRhK-4 cells were infected under one-step growth conditions in order to quantitate better differences in the kinetics of replication of different deletion mutants. At the permissive temperature (31° C.) in BS-C-1 cells, the replication of Δ131–144 virus (ts index, 1.8) was somewhat delayed compared with replication of the parental P16-pY1 virus or the large deletion mutant Δ96–137 (FIGS. 2A–C). The latter two viruses demonstrated similar replication kinetics, with virus yields approaching maximum by 72 hours postinoculation. In contrast, maximum yields of Δ131–144 were not reached until 144 hours postinoculation. This difference in replication kinetics was reflected also in the somewhat smaller size of Δ131–144 replication foci at 31° C. The higher intracellular virus titer immediately after adsorption of Δ131–144 (time 0, FIGS. 2A–C) likely reflects a higher multiplicity of infection in cells inoculated with the Δ131–144 virus.

At the nonpermissive temperature (37° C.), replication of Δ131–144 virus was further delayed, with no increase over input virus noted until after 72 hours postinoculation. Between 72 and 216 hours, the increase in the titer of Δ131–144 virus paralleled that observed between 18 and 72 hours at the permissive temperature (FIGS. 2A–C). In contrast, there was no difference in the growth kinetics of P16-pY1 and Δ96–137 viruses at 31° C. and 37° C., consistent with the low ts indices of these viruses (Table 1). The fact that the rate of intracellular accumulation of Δ131–144 virus between 72 and 216 hours at the nonpermissive temperature paralleled the rate of accumulation between 12 and 150 hours at the permissive temperature suggests that the ts phenotype of Δ131–144 might be due to a temperature-sensitive step occuring relatively early in the virus replication cycle. Additional one-step growth experiments confirmed that the replication of Δ131–144 virus was significantly delayed in comparison with P16-pY1 and Δ100–131 viruses at 35.5° C. in both FRhK-4 and BS-C-1 cells (data not shown). In general, in these one-step growth experiments, the final virus yield obtained with the ts Δ131–144 virus was similar to that obtained with the non-ts viruses.

Contribution of P2 region mutations to the ts phenotype. All of the deletion mutants described above were constructed in a background which included the P2 genomic region of the rapidly replicating, cytopathic strain, HM175/18f (see Methods). Thus, it was possible that the ts phenotype of the mutants described above might be derived in part from one or more of the numerous mutations present in the P2 region (S. Lemon, et al., *J. Virol.* 65:2056–2065 (1991)). To address this possibility, the P2 region from the cell culture-adapted HM175/P35 variant (pHAV/7) (J. Cohen, et al., *J. Virol.* 61:3035–3039 (1987)) was reintroduced into the ts cDNA clone pΔ131–144 to produce pΔ131–144/P2P35. Virus rescued from pΔ131–144/P2P35 RNA demonstrated a ts phenotype similar to Δ131–144 virus (data not shown), indicating that the ts phenotype was not codependent upon the presence of HM175/18f P2 region mutations. However, as expected, this virus replicated much more slowly than Δ131–144, requiring 2–3 weeks for demonstration of replication foci following RNA transfection, even at the permissive temperature.

Thermostability of ts virus particles. We compared the thermostability of the Δ131–144 virus with that of the P16-pY1 parent in order to determine whether the reduction in titer of this ts strain at the nonpermissive temperature might reflect increased thermolability of virions due to altered interactions between capsid proteins and genomic RNA. The infectious titers of the P16-pY1 and Δ131–144 viruses were reduced to a similar extent following brief incubation at temperatures ranging from 50 to 60° C. (FIGS. 2A–C). Thus the ts phenotype of Δ131–144 virus is not related to reduced thermostability of the virus.

Deletion mutation involving stem-loop IIb. All of the deletion mutations described above were located between stem-loop structures predicted to flank the pY1 region. To determine the impact of extension of these deletions in a 5' fashion into stem-loop IIb, an additional cDNA mutant (pΔ93–134) was constructed. Compared with the viable pΔ96–134 mutant, the deletion mutation in pΔ93–134 extends in a 5' direction by an additional 3 nt and includes the 3' terminal 2 nt of stem-loop (pseudoknot) IIb (FIG. 1). Multiple transfections of FRhK-4 or BS-C-1 cells with RNA derived from pΔ93–134, at either 31° C. or 35.5° C. failed to yield infectious virus (FIG. 1). In addition, a serendipitously discovered second-site cDNA mutant derived from the viable pΔ99–134 mutant which had an additional, random mutation involving a G-to-U substitution at nt 85, also failed to produce infectious virus after RNA transfection (data not shown). The G-to-U substitution at nt 85 would be predicted to destabilize the putative pseudoknot involving stem-loop IIb. These data suggest that retention of the secondary and possibly tertiary RNA structure in this region of the 5'NTR is essential for infectivity of the virus and provide further indirect support for the proposed structural model.

III. DISCUSSION

Virus mutants with deletions in the pY1 region which were rescued from transfected cells demonstrated two distinctly different replication phenotypes. Five mutant viruses with deletions ranging from 14 to 46 nucleotides in length and extending into the critical domain of nt 140 to 144 (Δ99–144, Δ116–144, Δ131–144, Δ96–140, and Δ96–141) were found to have a ts replication phenotype. If the entire sequence between nt 140 and nt 144 was removed, the resulting viruses were strongly ts (Δ99–144, Δ116–144, and Δ131–144). These viruses demonstrated a reduction in viral titer at the nonpermissive temperature (ts index) ranging from 1.8 to 3.6 $\log_{10}$ rfu/ml (Table 1). In contrast, a second group of mutant viruses with equally large deletions, up to 44 nucleotides in length, but not involving nt 140 to 144, replicated as efficiently as the parental virus at 37° C. and 31° C. These data indicate that the pY1 domain (nt 99 to 138) of HM175 virus is not required for replication in cultured cells, while the flanking single-stranded domain (nt 140 to 144) is essential for efficient replication at physiological temperatures. The marked difference between the ts index of the Δ99–144 mutant and those of the Δ116–144 and Δ131–144 mutants (3.6 versus 1.9 and 1.8 $\log_{10}$ rfu/ml, respectively, Table 1) demonstrates that the additional deletion of sequence elements within the pY1 domain (particularly nt 99 to 115) substantially enhances the ts phenotype of virus lacking nt 131 to 144. The critical ts domain (CUUGU, nt 140 to 144) is located at the 3' end of the pY1 tract. These nucleotides are part of a larger single-stranded segment which is accessible on the surface of the tertiary structure of the folded RNA, as evidenced by the ability of single-strand-specific RNases to cleave within the sequence spanning nt 135 to 152 (not shown). Although it is apparently not involved in base-pairing interactions with other regions of the 5'NTR, this short segment, especially the trinucleotide sequence UGU (nt 142 to 144), is very well conserved among different hepatovirus strains.

Large pY1 tract deletions which did not involve the critical nt 140 to 144 domain had no apparent effect on the replication of virus in FRhK-4 or BS-C-1 cell cultures maintained at physiologic temperatures (Table 1). Note the presence of smaller pY1 deletions in the sequences of other hepatovirus strains (FIG. 4). The sequence of several of these strains, MBB (A. Paul, et al., *Virus Res.* 8:153–171 (1987)), CF53 and PA21 (E. Brown, et al., *J. Virol.* 65:5828–5838 (1991)) was obtained from RNA isolated from cell culture-adapted variants, and thus these deletions may have occurred during adaption and passage in cultured cells. As shown in FIG. 1, a 4-nt deletion (nt 131 to 134) is known to have occurred in this domain during adaptation and passage of the HM175 strain in cell culture (J. Cohen, et al., *Proc. Natl. Acad. Sci. USA* 84:2497–2501 (1987)).

The foregoing is illustrative of the present invention, and not to be construed as limiting thereof. The invention is defined by the following claims, with equivalents of the claims to be included therein.

That which is claimed is:

1. A live hepatitis A virus deletion mutant having a deletion mutation in the 5' nontranslated region of the viral genome, wherein said deletion mutation is selected from the group consisting of:
   (a) Δ99–115 deletion mutants;
   (b) Δ99–130 deletion mutants:
   (c) Δ142 deletion mutants;
   (d) Δ143 deletion mutants;
   (e) Δ144 deletion mutants;
   (f) Δ141–142 deletion mutants;
   (g) Δ142–143 deletion mutants;
   (h) Δ143–144 deletion mutants;
   (i) Δ141–143 deletion mutants;
   (j) Δ143–144 deletion mutants;
   (k) Δ140–144 deletion mutants;
   (l) Δ96–141 deletion mutants;
   (m) Δ99–144 deletion mutants;
   (n) Δ116–144 deletion mutants; and
   (o) Δ131–144 deletion mutants.

2. A cDNA encoding a virus according to claim 1.

3. A method for inducing protective immunity against hepatitis A virus in a subject, comprising:
   administering to said subject an infectious, immunogenic, hepatitis A virus carrying an attenuating mutation, said virus being administered in an amount effective to induce protective immunity against hepatitis A virus, and said attenuating mutation being a deletion mutation in the 5' nontranslated region of the viral genome, wherein said deletion mutation is selected from the group consisting of:
   (a) Δ99–115 deletion mutants;
   (b) Δ99–130 deletion mutants;
   (c) Δ142 deletion mutants;
   (d) Δ143 deletion mutants;
   (e) Δ144 deletion mutants;
   (f) Δ141–142 deletion mutants;
   (g) Δ142–143 deletion mutants;
   (h) Δ143–144 deletion mutants;
   (i) Δ141–143 deletion mutants;
   (j) Δ143–144 deletion mutants;
   (k) Δ140–144 deletion mutants;
   (l) Δ96–141 deletion mutants;
   (m) Δ99–144 deletion mutants;
   (n) Δ116–144 deletion mutants; and
   (o) Δ131–144 deletion mutants.

4. A method according to claim 3, wherein said administering step is carried out by orally administering said virus to said subject.

5. A method according to claim 3, wherein said administering step is carried out by parenterally injecting said virus into said subject.

6. A vaccine formulation useful for inducing protective immunity against hepatitis A virus, comprising, in a pharmaceutically acceptable carrier, an infectious, immunogenic, hepatitis A virus carrying an attenuating mutation in an amount effective to induce protective immunity against hepatitis A virus, said attenuating mutation being a deletion mutation in the 5' nontranslated region of the viral genome that is selected from the group consisting of:
   (a) Δ99–115 deletion mutants;
   (b) Δ99–130 deletion mutants;
   (c) Δ142 deletion mutants;
   (d) Δ143 deletion mutants;
   (e) Δ144 deletion mutants;
   (f) Δ141–142 deletion mutants;
   (g) Δ142–143 deletion mutants;
   (h) Δ143–144 deletion mutants;
   (i) Δ141–143 deletion mutants;
   (j) Δ143–144 deletion mutants;
   (k) Δ140–144 deletion mutants;
   (l) Δ96–141 deletion mutants;
   (m) Δ99–144 deletion mutants;
   (n) Δ116–144 deletion mutants; and
   (o) Δ131–144 deletion mutants.

7. A vaccine formulation according to claim 6, wherein said vaccine formulation is an oral vaccine formulation.

8. A vaccine formulation according to claim 6, wherein said vaccine formulation is a parenterally injectable vaccine formulation.

9. A vaccine formulation according to claim 6, wherein said vaccine formulation is an inhalation vaccine formulation.

* * * * *